(12) United States Patent
Towe

(10) Patent No.: US 9,693,708 B2
(45) Date of Patent: Jul. 4, 2017

(54) SYSTEMS AND METHODS FOR WIRELESS TRANSMISSION OF BIOPOTENTIALS

(75) Inventor: Bruce C. Towe, Mesa, AZ (US)

(73) Assignee: Arizona Board of Regents for and on Behalf of Arizona State University, Scottsdale, AZ (US)

( * ) Notice: Subject to any disclaimer, the term of this patent is extended or adjusted under 35 U.S.C. 154(b) by 596 days.

(21) Appl. No.: 12/598,871

(22) PCT Filed: May 2, 2008

(86) PCT No.: PCT/US2008/062450
§ 371 (c)(1),
(2), (4) Date: Mar. 2, 2010

(87) PCT Pub. No.: WO2008/137703
PCT Pub. Date: Nov. 13, 2008

(65) Prior Publication Data
US 2010/0198039 A1    Aug. 5, 2010

Related U.S. Application Data

(60) Provisional application No. 60/916,152, filed on May 4, 2007.

(51) Int. Cl.
*A61B 5/04* (2006.01)
*A61B 5/07* (2006.01)
(Continued)

(52) U.S. Cl.
CPC ............ *A61B 5/076* (2013.01); *A61B 5/0031* (2013.01); *A61B 5/0006* (2013.01);
(Continued)

(58) Field of Classification Search
CPC ... A61B 5/0031; A61B 5/14503; H01L 29/93; H01L 27/0808
(Continued)

(56) References Cited

U.S. PATENT DOCUMENTS 3,662,758 A    5/1972    Glover ............................ 607/40
3,727,616 A    4/1973    Lenzkes ......................... 607/59
(Continued)

FOREIGN PATENT DOCUMENTS

DE    196 17 102    10/1997
DE    198 53 752    8/2000
(Continued)

OTHER PUBLICATIONS

Sezen, Passive Wireless Sensing Strategies for High Frequency Biomedical Sensing Applications, University of Minnesota, Dec. 2006.*
(Continued)

*Primary Examiner* — Jacqueline Cheng
*Assistant Examiner* — Puya Agahi
(74) *Attorney, Agent, or Firm* — Norton Rose Fulbright US LLP

(57) ABSTRACT

The invention relates to wireless biotelemetry of low level bioelectric and biosensor signals by directly modulating the backscatter of a resonant circuit. Low level electrical analog or digital signals are directly applied to a resonant circuit containing a voltage-variable capacitor such as a varactor diode, that proportionally shifts the resonant frequency and so amplitude of radiofrequency backscatter in a way that represents analog bioelectric or biosensor waveform data. By strongly driving the resonant circuit with a radiofrequency source, a voltage variable capacitance can be caused to amplify the bio-signal level by a parametric process and so provide sufficient sensitivity to telemeter for low millivolt and microvolt level signals without additional amplification. A feature of the device is its simplicity and that it accomplishes both modulation and preamplification of low level sensor signals by the same variable capacitance circuit which reduces the device size and power consumption.

24 Claims, 3 Drawing Sheets

(51) Int. Cl.
  *H01L 29/93* (2006.01)
  *A61B 5/145* (2006.01)
  *H01L 27/08* (2006.01)
  *A61B 5/00* (2006.01)

(52) U.S. Cl.
  CPC ....... *A61B 5/14503* (2013.01); *A61B 5/14539* (2013.01); *H01L 27/0808* (2013.01); *H01L 29/93* (2013.01)

(58) Field of Classification Search
  USPC .............. 600/300, 302, 437, 481, 483, 484
  See application file for complete search history.

(56) References Cited

U.S. PATENT DOCUMENTS

| | | | |
|---|---|---|---|
| 3,735,756 A | 5/1973 | Richards et al. | 601/2 |
| 4,026,276 A * | 5/1977 | Chubbuck | 600/407 |
| 4,102,344 A | 7/1978 | Conway et al. | 602/17 |
| 4,177,800 A * | 12/1979 | Enger | 600/302 |
| 4,494,950 A | 1/1985 | Fischell | 604/66 |
| 4,515,167 A * | 5/1985 | Hochman | 600/549 |
| 4,524,774 A | 6/1985 | Hildebrandt | 607/62 |
| 4,561,443 A | 12/1985 | Hogrefe et al. | 607/31 |
| 4,628,933 A | 12/1986 | Michelson | 607/53 |
| 4,736,752 A | 4/1988 | Munck et al. | 607/152 |
| 4,741,339 A | 5/1988 | Harrison et al. | 607/2 |
| 4,750,499 A | 6/1988 | Hoffer | 607/116 |
| 4,837,049 A | 6/1989 | Byers et al. | 216/6 |
| 4,932,405 A | 6/1990 | Peeters et al. | 607/57 |
| 4,947,844 A | 8/1990 | McDermott | 607/57 |
| 5,016,635 A | 5/1991 | Graupe | 607/49 |
| 5,058,581 A | 10/1991 | Silvian | 128/419 |
| 5,070,535 A | 12/1991 | Hochmair et al. | 455/41.1 |
| 5,170,802 A | 12/1992 | Mehra | 607/126 |
| 5,215,088 A | 6/1993 | Normann et al. | 600/377 |
| 5,314,458 A | 5/1994 | Najafi et al. | 607/116 |
| 5,344,386 A | 9/1994 | Schaldach | 600/16 |
| 5,358,514 A | 10/1994 | Schulman et al. | 607/61 |
| 5,411,535 A | 5/1995 | Fujii et al. | 607/32 |
| 5,583,510 A | 12/1996 | Ponnapalli et al. | 343/700 MS |
| 5,626,630 A | 5/1997 | Markowitz et al. | 607/60 |
| 5,735,887 A | 4/1998 | Barreras, Sr. et al. | 607/60 |
| 5,769,875 A | 6/1998 | Peckham et al. | 607/48 |
| 5,776,171 A | 7/1998 | Peckham et al. | 607/48 |
| 5,861,019 A | 1/1999 | Sun et al. | 607/60 |
| 5,870,672 A | 2/1999 | Stoddard et al. | 455/410 |
| 5,957,851 A | 9/1999 | Hossack | 600/459 |
| 5,967,986 A | 10/1999 | Cimochowski et al. | 600/454 |
| 5,995,874 A | 11/1999 | Borza | 607/61 |
| 6,140,740 A | 10/2000 | Porat et al. | 310/322 |
| 6,141,588 A | 10/2000 | Cox et al. | 607/9 |
| 6,210,347 B1 | 4/2001 | Forsell | 600/593 |
| 6,231,516 B1 | 5/2001 | Keilman et al. | 600/485 |
| 6,239,664 B1 * | 5/2001 | Northam | H03B 5/326 331/116 M |
| 6,368,275 B1 | 4/2002 | Sliwa et al. | 600/437 |
| 6,445,953 B1 | 9/2002 | Bulkes et al. | 607/33 |
| 6,447,448 B1 | 9/2002 | Ishikawa et al. | 600/300 |
| 6,562,033 B2 | 5/2003 | Shah et al. | 606/41 |
| 6,628,989 B1 | 9/2003 | Penner et al. | 607/59 |
| 6,911,764 B2 | 6/2005 | Pelrine et al. | 310/328 |
| 7,024,248 B2 | 4/2006 | Penner et al. | 607/60 |
| 7,283,874 B2 | 10/2007 | Penner | 607/33 |
| 7,702,395 B2 | 4/2010 | Towe et al. | 607/48 |
| 7,765,013 B2 | 7/2010 | Blick et al. | 607/116 |
| 2002/0026228 A1 | 2/2002 | Schauerte | 607/122 |
| 2002/0120184 A1 | 8/2002 | Beck | 600/300 |
| 2002/0147388 A1* | 10/2002 | Mass et al. | 600/300 |
| 2004/0044393 A1 | 3/2004 | Yarden et al. | 623/1.2 |
| 2005/0027175 A1* | 2/2005 | Yang | 600/302 |
| 2005/0055073 A1 | 3/2005 | Weber | 607/99 |
| 2005/0113744 A1 | 5/2005 | Donoghue et al. | 604/66 |
| 2006/0161225 A1 | 7/2006 | Sormann et al. | 607/61 |
| 2006/0196277 A1* | 9/2006 | Allen | G01D 21/00 73/861.12 |
| 2006/0217782 A1* | 9/2006 | Boveja et al. | 607/45 |
| 2007/0239003 A1* | 10/2007 | Shertukde et al. | 600/437 |
| 2007/0270672 A1* | 11/2007 | Hayter | 600/309 |
| 2008/0082025 A1* | 4/2008 | Hughes et al. | 600/595 |
| 2008/0234594 A1* | 9/2008 | Brooks et al. | 600/513 |
| 2008/0234599 A1* | 9/2008 | Chiao et al. | 600/547 |
| 2009/0248112 A1 | 10/2009 | Mumbru et al. | 607/60 |
| 2009/0306738 A1 | 12/2009 | Weiss | 607/30 |
| 2010/0234922 A1 | 9/2010 | Forsell | 607/61 |

FOREIGN PATENT DOCUMENTS

| | | |
|---|---|---|
| DE | 10 2008 002 228 | 12/2009 |
| EP | 0 343 858 | 5/1986 |
| WO | WO 98/29030 | 7/1998 |
| WO | WO 00/13585 | 3/2000 |
| WO | WO 2004/016315 | 2/2004 |
| WO | WO 2004/105583 | 12/2004 |
| WO | WO/2005/033719 | 4/2005 |
| WO | WO 2008/137703 | 11/2008 |
| WO | WO 2010/135634 | 11/2010 |

OTHER PUBLICATIONS

Chatzandroulis et al., A Miniature Pressure System with a Capacitive Sensor and a Passive Telemetry Link for Use in Implantable Applications, Journal of Microelectromechanical Systems, vol. 9, No. 1, Mar. 2000.*

Huang et al., A 0.5-mW Passive Telemetry IC for Biomedical Applications, Journal of Solid-State Circuits, vol. 33, No. 7, Jul. 1998.*

Helmeste, Passive RFID sensors, college senior design project, 2005.*

Saunders et al., Wireless Power and Data Transmission for in vivo Sensing, Rensselaer Polytechnic Institute.*

Chaimanonart et al., Two-Channel Data Telemetry with Remote RF Powering for High-Performance Wireless MEMS Strain Sensing Applications, Case Western Reserve University, 2005.*

Nambi et al., Radio Frequency Identification Sensors, Auburn University.*

Sezen et al., Passive Wireless MEMS Microphones for Biomedical Applications, Nov. 2005, University of Minnesota, vol. 127, pp. 1030-1034.*

Sezen et al., Passive Wireless MEMS microphones for biomedical applications, Nov. 2005, vol. 127, pp. 1030-1034.*

An abstract submitted for review to the BMES meeting in Houston, Texas, for presentation in Oct. 2002.

Englehart et al., "Classification of myoelectric signal burst patterns using a dynamic neural network," *IEEE*, pp. 63-64, 1995.

Gavrilov et al., "Stimulation of human peripheral neural structures by focus ultrasound," *Sov Phys Acoust*, 19(4)-334, 1974.

Haugland et al., "Skin contact force information in sensory nerve signals recorded by implanted cuff electrodes," *IEEE Trans. Rehab. Eng.*, 2(1):18-27, 1994.

Hiraiwa et al., "EMG pattern analysis and classification by neural network," *IEEE*, 1113-1115, 1989.

Hu et al., "Effects of low-intensity ultrasound on the central nervous system of primates," *Avist Space Environ Med*, 47(60):640-643, 1976.

Jang et al., "Using time frequency analysis technique in the classification of surface Emg signals," *IEEE*, 2: 1242-1243, 1994.

Matjacic et al., "Wireless control of functional electrical stimulation systems," *Artificial Organs*, 21(3):197-200, 1997.

Mayr et al., "EMG-controlled adjustment and fatigue monitoring in multi-channel surface stimulators," *Proceedings of the Second Annual IFESS Conference (IFESS'97) and Neural Prosthesis: Motor Systems*, 5 (NP'97), pp. 13-14, 1997.

Memberg et al., "A surgically-implanted intramuscular electrode for an implantable neuromuscular stimulation system," *IEEE Trans. Rehab. Eng.*, 2(2):80-91, 1994.

Mihran et al., "Temporally specific modifications of myelinated axon excitability in vitro following a single ultrasound pulse," *Ultrasound in Med Biol.*, 16(3):297-309, 1990.

(56) References Cited

OTHER PUBLICATIONS

Office Communication issued in U.S. Appl. No. 11/301,319, dated Oct. 18, 2007.
Office Communication issued in U.S. Appl. No. 11/301,319, dated Apr. 6, 2007.
PCT International Preliminary Report on Patentability issued in PCT/US2008/062450, dated Nov. 19, 2009.
PCT International Search Report and Written Opinion issued in PCT/US2008/062450, dated Sep. 22, 2008.
Phillips, William, "In vitro modification of nerve excitability via high frequency ultrasound pulses," Thesis presented in partial fulfillment of the Requirement for the Degree of Master of Science, May 2002.
Sawan et al., "Stimulator design and subsequent stimulation parameter optimization for controlling micturition and reducing urethral resistance," *IEEE Trans. Rehab. Eng.*, 4(1):39-46, 1996.
Takagi et al., "The actions of ultrasound on the myelinated nerve, the spinal cord, and the brain," *Jpn J Physiol.*, 10:183-193, 1959.
Towe et al., "Wireless Implantable Micro-Biosensors," ASU Departments of Bioengineering, Chemistry, Electrical Engineering, Jul. 22, 2003.
Towe, "Passive Backscatter Biotelemetry for Neural Interfacing," *IEEE*, Feb. 15, 2007.
U.S. Appl. No. 61/352,639 entitled "Apparatus, Systems, and Methods for Neurostimulation and Neurotelemetry Using Semiconductor Diode Systems," by Bruce C. Towe, filed Jun. 8, 2010.
Velling et al., "Modulation of the functional state of the brain with aid on focused ultrasonic action," *Ultrasound in Med Biol*, 16(3):297-309, 1990.
Wells, P.N.T., *Biomedical Ultrasonics*, Academic Press, London, p. 15, 1977.
Extended European Search Report in Application No. 08755017.4-1660/2152149 dated Apr. 11, 2013.

* cited by examiner

*Frequency 500 kHz/Division with Center Frequency at 265 MHz*

*Time Scale 200 Milliseconds per Major Scale Division*

SYSTEMS AND METHODS FOR WIRELESS TRANSMISSION OF BIOPOTENTIALS

CROSS-REFERENCE TO RELATED APPLICATIONS

This application is a national phase application under 35 U.S.C. §371 of International Application No. PCT/US2008/062450 filed May 2, 2008, which claims priority to U.S. Provisional Patent Application Ser. No. 60/916,152 filed on May 4, 2007. The entire contents of each of these applications are incorporated herein by reference.

BACKGROUND OF THE INVENTION

1. Technical Field

The present invention relates generally to biomedical engineering and, more particularly, to systems and methods for wireless detection and communication of bioelectrical signals.

2. Description of Related Art

Electrical waveforms that carry information about the function of the heart, brain, and nervous system are useful to physicians and researchers. These electrical signals are unique in that they are naturally in the low millivolt and tens of microvolt range. They are recorded in medicine and electrophysiological research using high impedance biopotential electrodes. The use of body-invading wires to carry outside such signals from inside living things is undesirable since the wires become sites for infection as they pass through the skin and create other practical problems of breakage. Accordingly, the inventors hereof have recognized a need for systems and methods for wirelessly detecting and transmitting amplitude and waveform information from low level bioelectrical signals originating from inside the body of living things to a remote base station receiver.

There are new generations of microminiature biochemical and biophysical sensors such as for pH, pressure, and temperature, osmolarity, becoming available which would desirably be placed wholly inside the human body for remote readout. Again, with the advent of these devices the inventor hereof has found a need to communicate their signals wirelessly with the exterior of the body.

Electrical circuitry typically used to detect and transmit biosignals has required the use of high input impedance preamplifiers to boost signal levels so that they are suited to modulating transmitter and oscillator circuits of various types that might be implanted into living things. A requirement is that biotelemetry devices implanted within the human body do not use batteries but rather use passive or inductive powering techniques where incoming RF energy is rectified for powering the needs of the circuitry. The present art requires relatively complex circuitry and consequently occupies larger volumes compared to those desired for implantation in living things with minimal invasiveness. Biotelemetry devices known to the present art have been on the order of cubic centimeter volumes, and required techniques of invasive surgery to implant devices.

The inventors hereof have recognized that it be desirable to telemeter bioelectrical waveforms using devices small enough to be introduced or injected into the body through a syringe needle lumen. Unfortunately, there have been problems in reducing the size of telemetry circuits to such small sizes. There are many reasons for this but mostly they stem from the complexity of circuitry needed to transform impedances, preamplify, and modulate the bioelectrical signals onto radiofrequency signals. The present state of the art consists of using conventional semiconductor FET and transistor amplifiers to accommodate high impedance bioelectrodes and then modulating these amplified signals onto the carrier wave of small but otherwise conventional radio transmitters of various sorts. These circuits usually require methods of rectifying power from an external RF source in order to power the amplifiers and oscillator circuitry. The overall result is that wireless telemetry of low level electrical signals has required circuitry occupying significant silicon chip sizes which are undesirably large, and which require surgery to introduce into the human body.

The inventors hereof have thus devised an approach of wirelessly telemetering bioelectrical and biosensor signals that would permit very small sizes of device and would be minimally invasive and passive in design. Exemplary embodiments of the invention demonstrate the ability to wirelessly telemeter bioelectrical and biosensor signals using a passive resonant circuitry approach that provides the capabilities of impedance transformation, modulation, and radio transmission in a very simple circuitry approach suited to very small package sizes and so minimally invasive. This invention is related but not the same as techniques of the field known as RFID technology.

The communications technology broadly known as RFID is based on the property of resonant circuits whereby an electrically resonant circuit will absorb power from a nearby transmitter frequency to which it is tuned. A review of the art has been authored by K. Finkenzeller in his book RF ID Handbook, (John Wiley and Sons Inc. New York, USA) and is incorporated by reference in this document. This is a process involving the mutual coupling of inductive circuits and the concept of reflected impedance change from a remote unit to a base unit. Variations in reflected impedance is equivalent to a change in electrical loading of the base unit transmitter. This is registered by monitoring a voltage change across the transmitter resonant circuit. This voltage typically decreases as a result of increased power transfer to the remote resonant circuit and this only happens when the remote unit is in frequency resonance with the base unit. Thus, there can be an identification of the presence of a circuit tuned to the specific frequency since no reflected impedance change will occur if there is an off-resonance condition.

The process of reflected impedance occurs at frequencies that are approximately below about 30 MHz where coupling between the base transmitter and remote unit are mostly inductive. A variation on this process that is often used at higher frequencies above about 30 MHz and upward into the microwave frequency region is known as the backscatter approach. The remote resonant system is modeled as resonantly absorbing RF energy from a high frequency transmitter and re-radiating the energy causing a remote receiver to see a change in RF intensity. This change in RF backscattered intensity detected at the base unit is indicative of the local presence of a resonant circuit tuned to the transmit frequency and constitutes an identification of the circuit.

A variation of this communication approach involves the use of variable capacitance diodes incorporated into resonant circuits such that the varying capacitance of the diodes cause phase modulation as disclosed in U.S. Pat. No. 7,158,010 by Fischer et al. The use of varactor diodes also causes the emission of harmonics of the fundamental as described by Finkenzeller (op cit.). These harmonics are useful in that they can be detected and demodulated for signal information but do so at a frequency that is different from the transmitted frequency fundamental. This makes detection of the reradiated signal easier since there is no competition or interference from the fundamental frequency which is emitted from the base unit transmitter.

A more sophisticated variation of this approach is to communicate digital information by using a logic circuit that modulates the resonant frequency of the remote circuit such that it time-varies its reflected impedance or backscatter efficiency. The on-off resonance of the circuit controlled by a logic circuit can communicate to base unit digital information that uniquely identifies the circuit or information stored in logic memory. The digital logic circuitry itself can be powered by an integral battery, or if the remote circuit is close to the base unit, typically within less than a decimeter, it can rectify the incoming RF energy and use it to power logic circuits.

This prior art is directed towards identification and transmission of stored digital information by wireless methods where the battery-less and self-powered aspect of the technology permits the use of small cards and easily read formats for storage of medical records, banking and commerce, and similar purposes. Small glass encapsulated digital RFID devices for identifying animals are well known.

However, the use of resonant coupling techniques for transmission of analog information has not yet been explored. Sensors are known whereby the measured parameter, such as pressure or temperature, directly affects the tuning of the resonant circuit usually by the change of a physical parameter such as capacitor plate spacing with pressure, and hence can modulate reflected impedance or backscatter in an analog proportional way. There have also been hybrid techniques whereby amplifiers have been used with sensors and low level biopotentials to transform their typically high impedance and boost signal levels to the point where modulation of passive resonant circuits may occur. For example, Towe in 1986 demonstrated a resonant coupling method of electrocardiogram (ECG) telemetry by using high impedance preamplifiers to boost the 1 millivolt ECG to about 500 millivolts and then applying the signal through a transistor to modulate the resonance of a tuned circuit in an amplitude-proportional way. The analog signal could then be recovered at a remote base station. The preamplifiers however had the problem of requiring batteries to power the on-board amplifiers and so only used the passive resonant coupling aspect to increase battery life.

Electrical signals originating from certain types of biochemical sensors such as Nernst-type pH electrodes, are both low millivolt level and very high impedance sources, typically above about 10 megohms. For telemetry of these kinds of signals from miniature sensors using passive resonant circuit technologies, the present state of the art requires the use of buffer preamplifiers to match circuit impedances of other components and preamplifiers. These occupy space and have the requirement for on-chip dc power of the amplifiers. This is a problem in that it increases the device size and complexity and so is undesirable for minimal invasiveness into the human body.

Thus it is the purpose of this invention to provide a method for avoiding the problems of preamplification and impedance transformation of bioelectrical and biosensor signals in order to allow them to more directly and simply modulate RF backscatter produced by a simple resonant circuit system.

SUMMARY OF THE INVENTION

The present invention provides systems and methods that cause a low level analog signal from bioelectrical or biosensors to modulate the amplitude of RF backscatter whereby the RF originates from an external radiofrequency source. The said backscatter from the circuit is thereby remotely detected and demodulated to recover the modulating signal. Backscatter modulation of an applied radiofrequency signal is caused by a method of applying said analog signal across a voltage variable capacitance within a circuit comprised of a voltage variable capacitance, inductance, and an isolating choke or resistor as illustrated in FIG. 1.

Certain embodiments comprise an apparatus comprising an electronic circuit configured to provide an inductance and a variable capacitance. The electronic circuit may be configured to receive an excitation signal and an analog sensor signal, and may have a resonant frequency that varies in response to a biosignal. The electronic circuit may be configured to transmit a response signal when the electronic circuit receives the excitation signal and the biosignal, and a characteristic of the analog signal can be determined by measuring the response signal.

In certain embodiments, the biosignal can be generated by a sensor selected from the group consisting of: a chemical, biochemical, magnetic, electromagnetic, physiological, and mechanical sensor. In specific embodiments, the electronic circuit may be configured to transmit the response signal wirelessly. The characteristic of the analog signal may be an amplitude of the analog signal, and/or a frequency of the analog signal.

In certain embodiments, the biosignal is generated by a biopotential. In specific embodiments, the excitation signal is a radio frequency signal. The excitation signal may be a digital logic signal in certain embodiments. In certain embodiments, the electronic circuit comprises an isolating resistor. The electronic circuit may be configured to receive a biosignal in vivo in specific embodiments. The electronic circuit may be configured to be implanted sub-cutaneously in a test subject. The electronic circuit may be configured to be inserted with a needle into the test subject, and in specific embodiments may be configured to pass through the lumen of a 1 millimeter syringe needle.

In certain embodiments, the electronic circuit is configured to be placed on the skin surface of a test subject. In specific embodiments, the electronic circuit comprises a pair of varactor diodes coupled back-to-back to form an equivalent series capacitance. Certain embodiments may also comprise a remote exciter configured to emit the excitation signal at a frequency equivalent to the resonant frequency of the electronic circuit when an analog sensor signal is not being applied to the electronic circuit. In specific embodiments, the excitation signal has a frequency between 30 MHz and 10 GHz, and in certain embodiments the excitation signal has a frequency between 100 MHz and 3 GHz. In specific embodiments, the excitation signal induces a voltage between 0.5 and 5.0 volts in the electronic circuit.

Certain embodiments may also comprise a method of measuring a biocharacteristic, the method comprising: providing an electronic circuit configured to measure a biopotential; providing an excitation signal to the electronic circuit; generating a biosignal with the biopotential and transmitting the biosignal to the electronic circuit; transmitting a response signal from the electronic circuit; and measuring the response signal to determine a characteristic of the biosignal. In certain embodiments, electronic circuit comprises a resonant frequency that is variable. In specific embodiments, the electronic circuit is configured to provide an inductance and a variable capacitance. In certain embodiments, the electronic circuit comprises a base resonant frequency when a biosignal is not transmitted to the electronic circuit, and wherein the excitation signal is provided at the base resonant frequency.

In specific embodiments, the biosignal is generated by a sensor selected from the group consisting of: a chemical, biochemical, magnetic, electromagnetic, physiological, and mechanical sensor. In certain embodiments, the characteristic of the biosignal is an amplitude and/or a frequency of the biosignal. Certain embodiments comprise implanting the electronic circuit in a test subject with a needle, and in specific embodiments, the needle may be hollow.

Certain embodiments comprise using a remote exciter to emit the excitation signal at a frequency equivalent to the resonant frequency of the electronic circuit when an analog sensor signal is not being applied to the electronic circuit. In certain embodiments, the excitation signal has a frequency between 30 MHz and 10 GHz, and in specific embodiments, the excitation signal has a frequency between 100 MHz and 3 GHz.

Certain embodiments comprise an apparatus of electronic components constituting a device such that a voltage variable capacitive reactance is coupled to an inductance forming a resonant circuit, wherein low level analog electrical potentials from high impedance bioelectrical or biosensor sources applied to this circuit will vary the said capacitive reactance and so change the resonance of said circuit in proportion to the amplitude of the analog waveform envelope.

In specific embodiments, the capacitive reactance is provided by at least one electronic component. In certain embodiments, the electronic component is a varactor diode. In specific instances, the capacitive reactance is provided by p-n junction capacitance.

Certain embodiments may be further defined as comprising a remote radio exciter tuned to the resonant frequency of the system of components such that sufficient signal is induced in the said inductance that the assembly will detectably backscatter the radio exciter signal as well as generate remotely detectable radio harmonics of said radio exciter.

Certain embodiments may be further defined as comprising a radio receiver that detects and demodulates the backscattered signals, the demodulation process following those techniques, wherein such methods may include direct conversion demodulation, AM, FM, or phase demodulation so as to reproduce the original modulation signal.

Specific embodiments comprise a method of using the device of claim 45, wherein the voltage variable capacitive reactance is electrically driven by an applied radio exciter signal known as a pump signal, of sufficient amplitude such that a device having time varying capacitance reactance in combination with the inductance forming a resonant circuit results in a parametric amplification of the electrical signal modulation according to principles of parametric amplification, the amplification process then substantially improving the sensitivity of the device to modulating signals.

Certain embodiments may comprise a method of generating a bias voltage needed for the proper electrical operating point of the variable capacitance by a method of summing the bioelectrical or biosensor input signal with an electrical offset potential, wherein the offset potential may be generated by a small conventional on-device battery generated by dissimilar metals constituting the two biopotential electrodes used to detect the bioelectrical signal, the said bias voltage naturally resulting from the use of electrode metals having dissimilar half-cell potentials. In specific embodiments, the device is implanted within the human body and connected to biopotential electrodes to telemeter bioelectrical signals originating from the heart, brain, and nervous system. In certain embodiments, the device is connected to a biochemical or physical sensor wherein signals from the sensor are wirelessly transmitted to a base station. In specific embodiments, the device is used to monitor the functions of brain electrical activity for the purposes of diagnosis and detection of neurological disorders of a bioelectrical nature such as epilepsy. In certain instances, the device is placed in or on the heart to monitor the bioelectrical activity of the heart for purposes of control of devices which control the heart rhythm and electrical functionality.

In exemplary embodiments, voltage variable capacitance devices such as varactor diodes exhibit a desirably high input impedance to electrical signals in the frequency ranges below about 100 kHz. This provides a minimal loading on biopotential electrodes or on sensors producing an electrical signal.

Another feature of this invention that lends to its high sensitivity and allows the omission of amplifiers in the device is the recognition that a relatively small voltage applied to the voltage variable capacitor (although causing only a small fractional change) can be detected with relatively high sensitivity since a small change in a numerically high value is still a large change in Hertz. In exemplary embodiments, the demodulation instrumentation is directly sensitive to Hertz. This can result in a high sensitivity to small bioelectrical and sensor signals without preamplification.

The inventors have made a significant technological advance in reducing the size and increasing the capability of potentially implantable micro-biotelemetry systems. The work the inventors propose here will advance the development of long-foreseen implantable biosensors that allow routine personal health monitoring by easily inserted into the body through syringe needles. Certain embodiments may monitor the heart and biochemical nature of tissue as a platform for research directed towards development of sophisticated sensors for blood and other body fluids. The potential military applications for implanted biosensors is quite extensive. Biosensors could give an instant assessment of soldier physiologic condition, pre-symptomatic warnings of exposure to biohazards, rapid battlefield medical diagnosis, and be a critical part of a drug delivery system that administers antidotes subsequent to blood detected indicators of toxic exposures. Certain embodiments may comprise practical micro-biochips a millimeter and less in size. The inventors propose projects that will lead to the manufacture of ECG and pH implantable biosensors. Implantable microchips that monitor the physiological status of the body and blood then telemeter to a local or remote read-out may be beneficial in many medical applications. Such microdevices are widely recognized as having the potential to lead revolutions in the speed, accuracy, and sensitivity in the assessment of the condition of the human body. Implanted microsensors would provide rapid and highly localized methods of monitoring blood and functions of organs.

The inventors have fabricated prototypes of a passive biotelemetry devices nearing the size where they could be introduced into the body with minimal trauma and approaching that which could be routinely performed using syringe needles. The biotelemetry system is so sensitive to millivolt-order signals that it can easily telemeter the electrocardiogram. The range of the implants is rather limited and depends on their design and size. The range is sufficient to transmit from inside the body to a worn receiver, generally momentarily held or worn over top of the implanted biosensor. The external device both powers and detects the sensor signal. The biosensor signals would be relayed to a personal readout device that could be networked using conventional technologies.

The inventors propose the development of a class of biosensors that initially monitor physical condition through parameters such as ECG and tissue pH. There are two types of biosensors for which the inventors have preliminary data, including: (1) electrocardiography—for introduction under the skin in the arm or chest area, to allow instant monitoring of the heart by a hand-held device without placement of skin electrodes; and (2) pH—for sensitive physiologic status monitoring. Blood and tissue pH, measured with sufficient accuracy, are a sensitive indicator of infection, fatigue, incipient physiological shock, and a presymptomatic indicator of exposure to harmful agents.

Certain embodiments may also comprise additional classes of sensors through a process of coupling known principles to the biotelemetry system. These include, for example: (1) osmolarity—of blood and tissue is of great interest for its strong relationship to blood glucose levels. It also reflects dehydration and levels of stress; (2) temperature—as an indicator of excessive desert sun exposure, infection, or overexertion; (3) blood pressure—as a general indicator of physical condition and/or degree of nervous stress; (4) chemistries—of the blood and tissue of which there are a potentially large number including hormones; and (5) bioelectrical activity—at microvolt levels of sensitivity for its indications of brain and neural function.

In certain specific embodiments, the inventors believe these chips to have particular application in rapid assessment of soldier physical and physiologic condition and possibly in detecting presymptomatic infection or toxic exposure. In cases where a soldier may be injured, the inventors envision that medical personnel would be able to place a hand held reader over an implanted microchip and immediately and without electrode application record the soldier's ECG and assess the potential for physiologic shock as reflected in blood pH. Implanted microsensors have the potential for indicating presymtomatic exposure to infectious or chemical agents and to actuate personal drug delivery systems to administer antidotes.

The sensor information could be used, for example to: (1) monitor the heart ECG and potentially transmit other neuroelectrical waveforms; (2) assess degree of soldier injury through its effects on blood chemistry; (3) determine the potential for physiologic shock after injury; (4) show a presymptomatic response to biological infection or to hazardous agents; (5) determine the level of a soldier's operational readiness and level of fatigue. In certain embodiments, the inventors propose new classes of implantable micro-biosensors.

There have been developed during preliminary work a number of different biotelemetry prototypes of varying size and range developed. They range from bread-board versions of about 6 mm square having decimeter-order ranges, to versions 1 mm×3 mm long, have several centimeter range. The smallest of the devices could be introduced into subcutaneous tissue, positioned near blood vessels, or located near any specific organ or tissue in the body by the use of reasonably sized introducers.

The inventors have developed a new biotelemetry approach using re-radiating parametric amplifier technology operating at high frequencies in combination with phase sensitive receiver designs. Parametric-effect devices are based on the use of time-varying reactances for amplification, frequency up-conversion and down conversion, and oscillators at microwave frequencies. Parametric devices transfer the power from an RF pump frequency to the signal frequency, as opposed to standard amplifiers that transfer power from the dc source to the signal frequency. Manley and Rowe have published the standard reference on parametric amplifiers. FIG. 4 shows an ECG used as a sensor test signal telemetered over a half-meter distance by using this approach with a 1.5 cm antenna.

A significant realization in this work is that RF pumped parametric amplifiers under certain circumstances exhibit not only substantial gains (>20) with few components, but re-radiate a signal that is amplitude and phase modulated by very small electrical signals. A parametric-based telemetry circuit comprising three discrete components exhibits a remarkable number of useful electrical characteristics. These include a high unamplified sensitivity to microvolt level signals, a high input impedance ($>10^7 \Omega$) and an analog bandwidth in the dc to Megahertz range. The high input impedance is of particular interest since it makes the device essentially an electrometer-amplifier of the type needed for high stability potentiometric measurements.

In certain embodiments, each microtelemetry device has the potential to easily operate at any carrier frequency in the range of 100 MHz to 3 GHz by simple inductor modifications. It is possible to use multiple carrier frequencies as a means to many simultaneous sensor channels. Existing embodiments can currently telemeter bioelectrical waveforms as low as about 30 microvolts.

These microchips have a range of about 20-30 times their antenna diameter (about 5 cm range in this case) and require no power. This is sufficient for transmitting the short distance through the body to a surface worn readout. The inventors envision a very low power worn biotelemetry exciter-receiver that requires minimal power dissipation; perhaps a wrist display or flexible display worn on clothing. The system might also take good advantage of antennas woven into the fabric of uniforms and clothes under development by other groups.

The high input impedance of the microtelemetry system allows its direct interface to potentiometric sensors. FIG. 5 is preliminary data showing the use of the microtelemetry system to transmit a pH signal from a small glass pH electrode. The pH electrode was immersed in calibrated buffers and electrically connected to the input of the microtelemetry system. A remote receiver loop a half meter away received and recorded the changing pH. Although slightly nonlinear due to the relatively large (several hundred millivolt) pH signal, the plot shows the ability of the telemetry system to directly interface with high impedance electrodes without further preamplification.

The inventors envision that the certain embodiments will incorporate potentiometric technologies to sense local tissue or blood pH with the potential for expansion of application to other biochemistries of interest. In certain exemplary embodiments, pH electrodes can be made by coating a thin film of a noble metal and depositing pH sensitive glass, silicon dioxide, silicon nitride and sometimes layers of the two a fraction of a micron thick.

Embodiments of the invention may be packaged in biocompatible materials that minimize biological inflammatory responses, integrate well with tissue, and resist humidity penetration. In specific embodiments, glass and ceramic packages or various encapsulating polymers may be used.

In one embodiment, an apparatus of electronic components constituting a device such that a voltage variable capacitive reactance is coupled to an inductance forming a resonant circuit. Low level analog electrical potentials from high impedance bioelectrical or biosensor sources applied to this circuit will vary the said capacitive reactance and so change the resonance of said circuit in proportion to the amplitude of the analog waveform envelope. For example, the capacitive reactance can be provided by electronic components such as varactor diodes. Additionally or alternatively, the capacitive reactance is provided by the p-n junction capacitance.

In another embodiment, an apparatus comprises device as described above in combination with a remote radio exciter tuned to the resonant frequency of the system of components such that sufficient signal is induced in the said inductance that the assembly will detectably backscatter the radio exciter signal as well as generate remotely detectable radio harmonics of said radio exciter. A radio receiver may be combined with this apparatus for detects and demodulates the backscattered signals. The demodulation process may be performed using, for example, direct conversion demodulation, AM, FM, or phase demodulation so as to reproduce the original modulation signal.

In yet another embodiment, a voltage variable capacitive reactance is electrically driven by an applied radio exciter signal known as a pump signal, of sufficient amplitude such that the device time varying capacitance reactance in combination with the inductance forming a resonant circuit results in a parametric amplification of the electrical signal modulation. This amplification process then substantially improving the sensitivity of the device to modulating signals.

In still another embodiment, a method comprises generating a bias voltage needed for the proper electrical operating point of the variable capacitance by summing the bioelectrical or biosensor input signal with an electrical offset potential. This offset potential may be generated by a small conventional small on-device battery or by dissimilar metals constituting the two biopotential electrodes used to detect the bioelectrical signal. The said bias voltage naturally results from the use of electrode metals having dissimilar half-cell potentials.

In another embodiment, a device is implanted within the human body and connected to biopotential electrodes to telemeter bioelectrical signals originating from the heart, brain, and nervous system. As such, the device may be used to monitor the functions of brain electrical activity for the purposes of diagnosis and detection of neurological disorders of a bioelectrical nature such as epilepsy. The device may also be placed in or on the heart to monitor the bioelectrical activity of the heart for purposes of control of devices which control the heart rhythm and electrical functionality. Additionally or alternatively, the device may be connected to a biochemical or physical sensor wherein signals from the sensor are wirelessly transmitted to a base station.

It is an object of this invention to provide a method of increasing the sensitivity of the achieved backscatter modulation by an applied analog signal by employing the method of parametric amplification. This is achieved by the method of causing the voltage variable capacitance to undergo a relatively large periodic change at the frequency of the applied radiofrequency source. This method is accomplished by driving said resonant circuit by an applied radiofrequency signal in the range of 30 MHz to 10 GHz but preferably in the range of 100 MHz to 3 GHz, such that a voltage in the range of 0.5 volts to 5 volts in value at a radiofrequency rate is induced on the circuit inductance. This method causes the voltage variable capacitance device such as a varactor diode, to undergo a sufficient change such that the resulting analog signal modulation applied to the variable capacitance is thereby increased by a process of parametric amplification by the resonant circuit.

The parametric gain of the said resonant circuit will depend on the level of radio exciter amplitude and hence the variation in the base value of said variable capacitance. The gain desirably can be in the range of slightly greater than 1 one to as high as 10 but preferably in the range of 5 to 8 to avoid instability and tendency towards self-oscillation of the resonant circuit. By this method, the signal will cause a larger change in the remotely detected demodulated signal than would occur at RF driving levels that are lower than approximately 0.5 volts.

In another embodiment, this invention may employ a bias voltage level in the range of 0 to 1 volt placed electrically across the said voltage variable capacitances. This bias voltage level may be useful in establishing the operating point of voltage variable capacitances, such as certain varactor diodes, as required by their construction and manufacture. This bias voltage level may be conveniently obtained using the offset potential of two dissimilar metals used as biopotential electrodes as is known to electrochemists or may be obtained by a small battery in series with the electrodes.

A feature of this system is that impedance transformation, preamplification, as well as modulation of RF backscatter can be effected by a relatively simple circuit involving few electrical components.

It is another feature of this system that it has sufficient sensitivity for telemetry of biopotentials from electrodes used in neurointerfacing to the heart, brain, and nervous system in the low tens of microvolt range as commonly employed by electrophysiologists and neuroengineers.

It is another feature of this invention in that it can have an exceptionally wide signal bandwidth ranging from direct current levels to hundreds of kilohertz to MegaHertz.

It is another feature of this invention that the device does not require the conversion of applied RF energy to direct current to power conventional amplifiers ordinarily needed to boost the amplitude of low level signals.

It is another feature of this invention that bioelectrical and biosensor analog signal levels can be modulated on the RF backscatter and their waveforms recovered by conventional techniques of RF backscatter demodulation.

It is another feature of this system that because if its electrical simplicity the remote unit size can be reduced to a scale such that the device can be implanted into the human body through the lumen of small needles such as commonly used in medical applications rather than surgery and so minimize the trauma of such introduction.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF INVENTION

Figure 1:
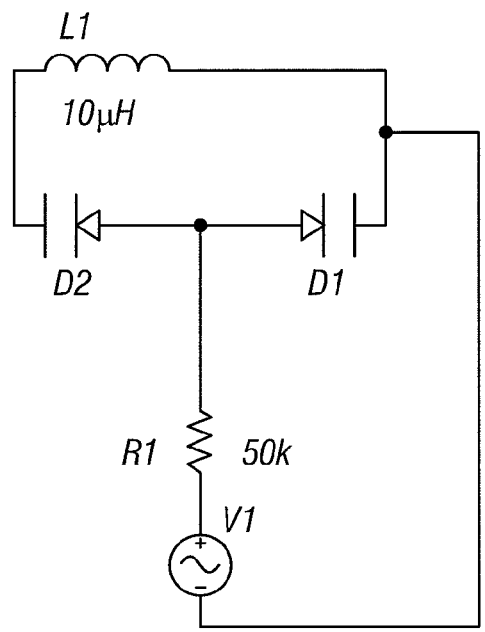
FIG. 1. Schematic of the passive biotelemetry system. V1 models the input signal originating from biopotentials or biosensors. R1 is an isolating resistance and D1 and D2 represent back-to-back connected varactor diodes used as variable capacitances. L1 is the inductor forming a resonant circuit and also serves as an antenna.

This invention relates to the field of radio communication devices that use the coupling of tuned electrically resonant circuits to carry information between a remote unit and a base station. In one embodiment, a remote unit is of an electrically passive design containing no batteries and deriving its power needs from the incoming radio frequency carrier wave. This allows the manufacture of biopotential communication devices that have small size and potentially long lifetimes. Since there are no batteries to wear out, they are suited to tasks such as wireless telemetry of bioelectrical and sensor data from small physical or chemical sensors implanted in the body of humans or other living things.

Certain embodiments of the invention employ the principle whereby small voltages applied to resonant circuits constructed with voltage variable capacitances will shift resonant frequencies by a small percentage amount of the resonant frequency. At high operating frequencies in the UHF and microwave region, the absolute frequency change is a relatively large number of Hertz and so sensitively demodulated by conventional frequency demodulation techniques.

A second aspect of this invention is the aspect of preamplification of low level electrical signals by the parametric amplification that occurs by the circuit configuration of the voltage variable capacitors with an inductor forming a resonant circuit. Time varying capacitances arranged such that a signal voltage is applied across their capacitance will be amplified by a process of parametric amplification. This amplification occurs concurrently with the backscatter modulation of the applied RF carrier. Thus two processes, amplification and modulation, are accomplished at the same time by using the same time-varying capacitances with a minimum of electrical circuitry.

Another aspect of this invention is a circuit design using variable capacitance devices in a way that presents high input port impedance for modulating electrical signals originating from sources such as high impedance bioelectrodes and high impedance biochemical and biophysical sensors. This high input port impedance for parametric devices is advantageous since it allows direct connection of high resistance bioelectrodes and biosensors to the resonant circuitry without need for power-consuming impedance matching amplifiers or circuitry. This simplifies the circuitry even further over the use of conventional FET and transistor buffer amplifiers that would ordinarily be required to match high impedance signal sources.

Another aspect of this invention is the design of a telemetry system of wide bandwidth. This feature arises through the modulation method of applying signals directly across the voltage variable capacitors rather than the use of conventional FET or transistor circuitry prior to modulation and so would restrict bandwidths to that of these prior circuitry.

Another feature of this invention is that it allows a considerable miniaturization of the remote unit circuitry compared to the current art of integrated circuit design by virtue of its greatly reduced parts count compared to the usual FET amplifiers, RF power conversion circuitry, and often analog to digital conversion requirements as often is the case in current art.

Using components from commercial manufacturers, it is possible to achieve form factors that will pass through the lumen of a 1 mm syringe needle yet have sufficient range to telemeter biopotentials to an externally worn receiver. By a simple process of duplicating the simple circuit and shifting the frequency of each circuit it is possible to achieve multichannel operation.

Exemplary Electrical Circuit

In its simplest yet functional and illustrative configuration, the telemetry device employs a pair of varactor diodes in a half-bridge configuration and a miniature inductor to form a resonant circuit. An external RF exciter pumps energy into this system which the circuit then re-radiates on a different harmonic frequency. Electrical signals originating from high impedance sources such as biopotential electrodes or miniature chemical or physical sensors, are applied to the voltage variable capacitors through an isolating resistor or alternately an inductive choke to prevent loading of the resonant circuit by the signal source.

The frequency of operation as defined by the component values of the inductance and variable capacitances can encompass a wide range that is desirably but not limited to frequencies of above about 100 MHz and extending into the multiple-GHz microwave range with the appropriate choice of inductors and voltage variable capacitances.

This assembly of electrical components is a wireless biotelemetry device that utilizes the simple structure of an inductive-capacitive (LC) resonant circuit. In a typical configuration where the voltage variable circuit elements are varactor diodes, they are connected back-to-back to form an equivalent series capacitance. Their p-n junction capacitance can be controlled over a wide range such as 2 to 10 pF with typically 1-10 volts of applied voltage such as commonly found in data sheets from manufacturers such as the MA4ST2000 series made by Microwave Associates (Massachusetts, USA).

FIG. 1 shows the configuration of this circuit. Millivolt and microvolt order biopotential signals for example denoted by V1 are placed across the varactors D1 and D2 through an isolating resistor R1. The series varactors are in combination with inductance L1 to form a resonant circuit for a frequency preferably above about 100 MHz. This circuit is electrically excited by an external and remote RF pump source which induces as much as several volts across the diodes and inductor before saturation. At the same time, the small voltage V1 applied across the resonant circuit varies the baseline capacitance of the series diodes and hence vary the system fundamental resonant frequency.

High order harmonics of the pump frequency are naturally radiated from the diode-inductor in this circuit according to principles of nonlinear response of the diodes, and these harmonics propagate outward from the inductor and through space. These radiated harmonics are shifted slightly in frequency by the action of the modulating signal V1. The absolute frequency variation due to the modulating source is multiplied in by a factor that is the same as the harmonic number and so by detecting the frequency shift at higher harmonics there is a greater overall sensitivity to changes in V1.

Detection and frequency demodulation of the radiated harmonics can occur through common methods of radio communication, such as direct conversion, superheterodyne, FM, and slope detection AM demodulation schemes.

Changes in voltage across the varactor affects the frequency of both the fundamental resonance as well as the radiated harmonics. Even microvolt level signals can modulate the varactor diode capacitance to a remotely detectable degree by using conventional radio demodulation techniques. Operating frequencies are desirably in the UHF and GHz band to allow the more efficient use of small loop antennas on the device leading to compact size. Varactor-based L-C circuits are tunable to specific resonant frequencies. This lends to specific channels of operation and possible multichannel designs by an array of varactor circuits tuned to non-overlapping frequency bands.

Parametric Amplification

This invention employs the process of signal parametric amplification to boost sensitivity to low level microvolt level signals from bioelectrodes or biosensors. It has been long known that parametric amplifiers have in theory both an infinite input resistance and no Johnson noise and so are noiseless methods of amplification. Parametric amplifiers depend on a time varying circuit parameter, usually a capacitance to provide gain. The functioning of parametric amplifiers is a mathematically rigorous field of study and the reader is referred to references by Matthaei et al, and Sard et al., for examples.

Conventional parametric amplifiers employ a time varying capacitance by AC driving the junction of a varactor diode. An electrical signal applied to the junction of the diode can be increased in amplitude when the junction capacitance is forced to change in value by an electrical pump signal. Since $V=Q/C$, for a given signal charge Q, the potential V across the capacitor will increase to a larger value if C decreases. In our system, the junction capacitance of a varactor diode or similar volt-variable device is driven by an AC pump voltage. Biopotentials applied to the time varying capacitor shift its base capacitance and so this modulates the current flow in a companion inductive loop forming a resonant circuit.

Parametric amplification of the applied signal V1 occurs when the amplitude of the RF exciting signal is drives the varactor diodes to significant changes in capacitance at the excitation frequency. By this invention the signal frequency is converted to an RF frequency. The RF frequency amplitude and frequency modulation is relatively larger than is achieved when the varactor diodes are not driven to large capacitance excursions by the applied RF excitation.

Figure 2:
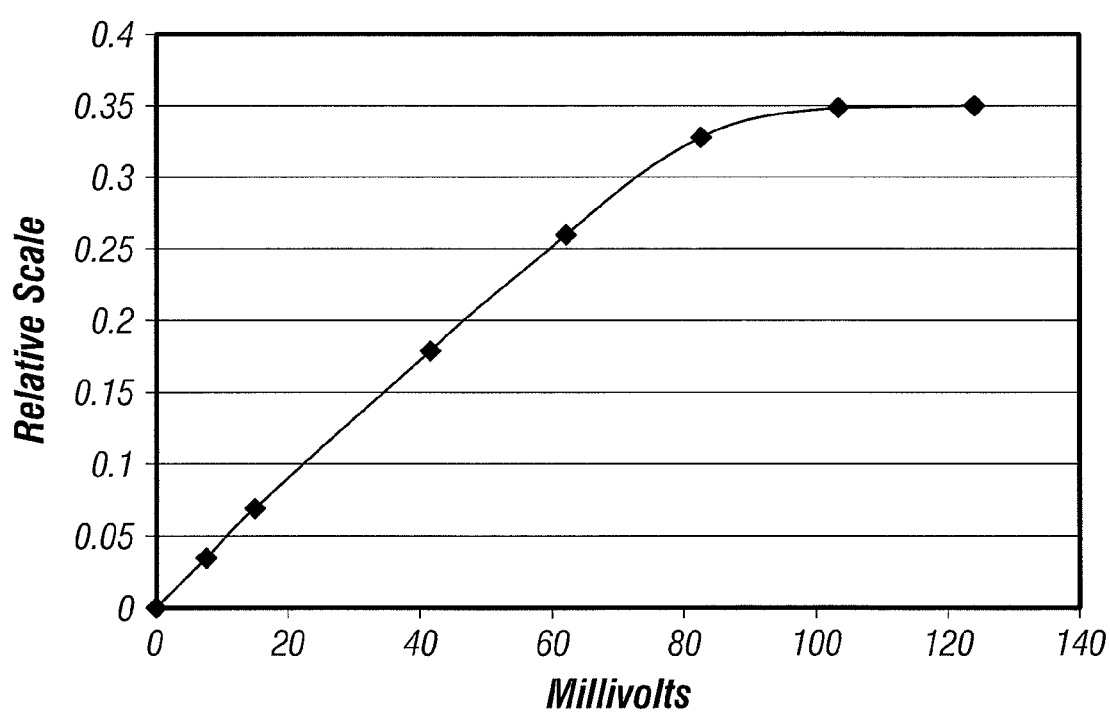
FIG. 2. Plot of the demodulated amplitude level resulting from a test 10 KHz electrical signal level (in millivolts) applied to the circuit in FIG. 1 and having a radio exciter frequency of 265 MHz.

FIG. 2 shows the level of remotely detected envelope amplitude modulation caused by a one millivolt sine wave applied as source V1 to the circuit in FIG. 1.

Figure 3:
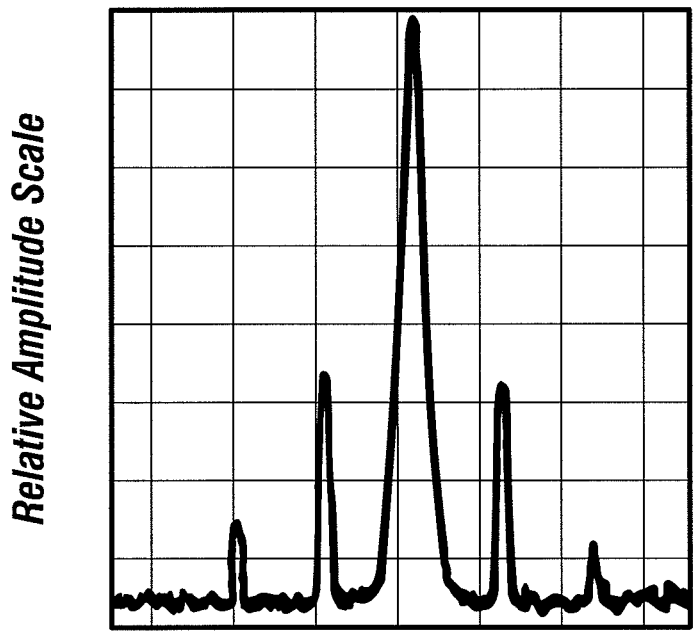
FIG. 3. Spectrum analyzer display of the backscattered signal from the circuit in FIG. 1 using a 1 millivolt 500 KHz modulating signal as V1. The spectrum analyzer output shows the wide achievable bandwidth through the appearance of expected AM sidebands at +/−500 KHz on either side of the carrier.

FIG. 3 shows the remotely detected spectrum of a backscattered signal with a 1 millivolt 500 kHz test signal used as the signal source V1. The bandwidth of the system is seen in this example to be much larger than the few kilohertz typically achieved with more conventional circuit designs targeted for implantable wireless telemetry systems and showing that it may transmit wide bandwidth digital data as well.

Figure 4:
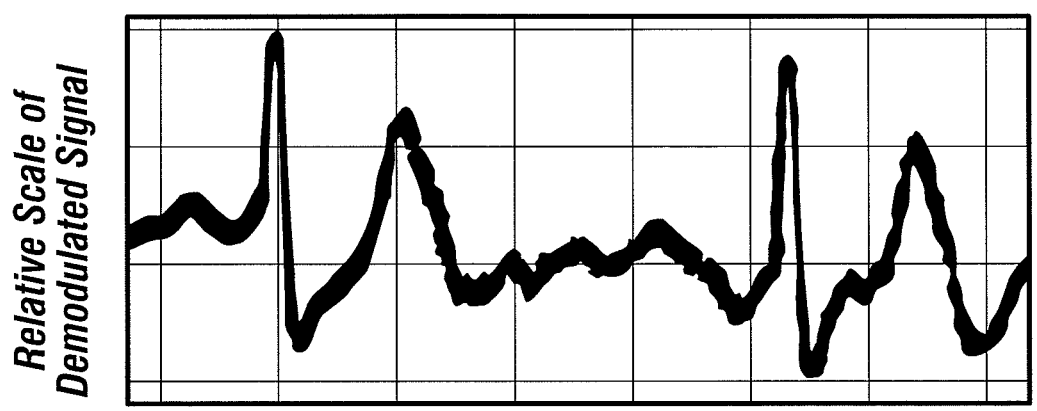
FIG. 4. A 1 mV ECG waveform detected by body surface electrodes telemetered over a half-meter distance using the circuit shown in FIG. 1 using a body surface ECG signal as input signal V1 originating from biopotential electrodes applied to the chest region of a human volunteer.

FIG. 4 shows the remotely demodulated signal using two silver silver-chloride surface electrodes attached to the human chest and the roughly 1 mV detected ECG biopotential used as V1 as in FIG. 1.

Figure 5:
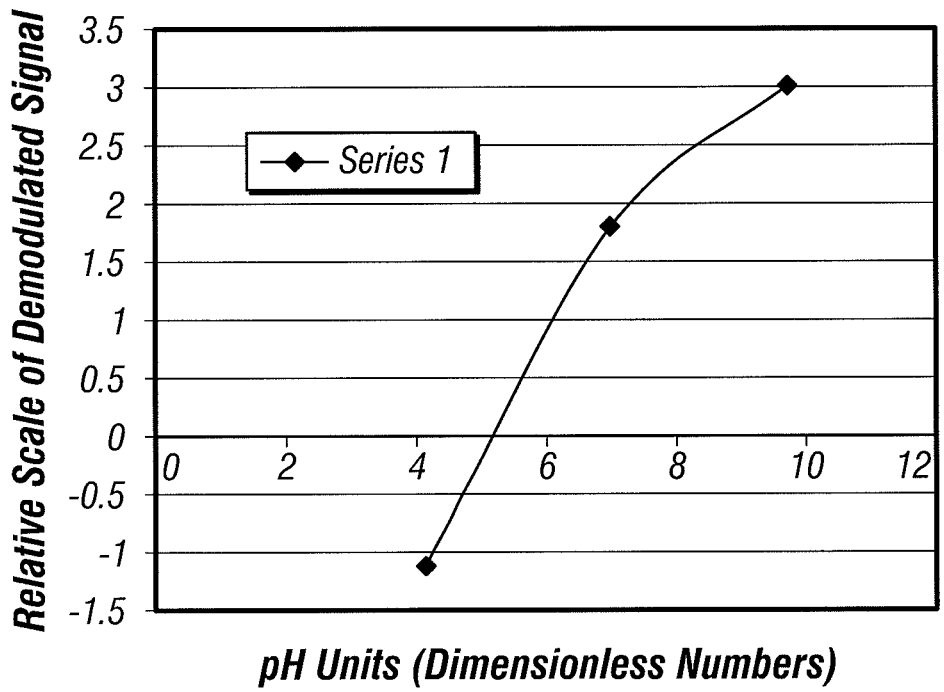
FIG. 5. Plot of the demodulated signal level originating from a commercial pH electrode connected as V1 in FIG. 1 and then exposed to a changing pH buffer calibration solutions of 4, 7, and 10.

FIG. 5 Shows the remotely demodulated signal obtained from using a commercial (VWR Inc.) ½" glass pH electrode bulb of conventional design and well known to chemists and connected up as the signal source V1. The electrode was exposed to pH calibration solutions at pH 4, 7, and 10. To detect steady dc levels from the pH sensor electrodes, the demodulator used a direct conversion synchronous demodulation scheme.

Figure 6:
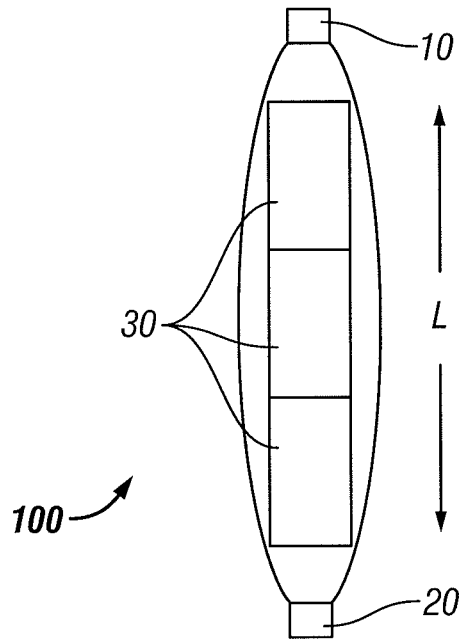
FIG. 6 Schematic drawing of a potentially injectable wireless pH sensor.

FIG. 6 illustrates a schematic of a potentially injectable wireless pH sensor 100. Sensor 100 comprises a pH sensitive electrode 10 and a reference electrode 20. Sensor 100 further comprises microtelemetry sections 30. In specific embodiments, microtelemetry section 30 has a length L that is approximately 3 mm. In certain embodiments, sensor 100 is approximately 1 mm or less in diameter. As s result, sensor 100 may be injected through the lumen of a 14, 16, or 18 gauge needle Certain aspects of the present invention are described in the white paper entitled "Wireless Implantable Micro-Biosensors" (submitted in consideration for DARPA BAA03-02) incorporated by reference.

While the present disclosure may be adaptable to various modifications and alternative forms, specific embodiments have been shown by way of example and described herein. However, it should be understood that the present disclosure is not intended to be limited to the particular forms disclosed. Rather, it is to cover all modifications, equivalents, and alternatives falling within the spirit and scope of the disclosure as defined by the appended claims. Moreover, the different aspects of the disclosed apparatus and methods may be utilized in various combinations and/or independently. Thus the invention is not limited to only those combinations shown herein, but rather may include other combinations, as well.

REFERENCES

The following references are incorporated by reference:

Heetderks, W., "RF Powering Of Millimeter- and Submillimeter-Sized Neural Prosthetic Implants," IEEE Transactions on Biomedical Engineering, Vol. 35, No. 5, 323. May 1988.

Matthaei, G. L., "A Study of the Optimum Design of Wide-Band Parametric Amplifiers and Up Converters," IRE Transactions on Microwave Theory Tech., Vol. MTT-10, pp. 23-28 January 1961.

Mohseni, P., K. Najafi, S. J. Eliades, and X. Wang, "Wireless Multichannel Biopotential Recording Using An Integrated Fm Telemetry Circuit," IEEE Transactions On Neural Systems And Rehabilitation Engineering, Vol. 13, No. 3, September 2005.

Sard, E., B. Peyton, S. Okwit, "A positive resistance up-converter for ultra-low noise amplification," IEEE Trans. Micro Theory Tech., Vol. 14, pp. 608-618, December 1966.

Towe, B. C., "Passive Biotelemetry by Frequency Keying," IEEE Transactions on Biomedical Engineering, Vol. BME-33, No. 10, October 1986.

Wise, K. D., D. J. Anderson, J. F. Hetke, D. R. Kipke, K. Najafi, "Wireless Implantable Microsystems: High-Density Electronic Interfaces to the Nervous System," Proceedings of the IEEE, Vol. 92, No. 1, January 2004.

U.S. Pat. No. 7,158,010 to Fischer et al.

The invention claimed is:

1. An apparatus comprising:
a completely passive electronic circuit having a varactor diode coupled to two electrodes configured to provide an inductance and a variable capacitance, wherein:
the electronic circuit is configured to receive an excitation signal and a biosignal, wherein the excitation signal has a frequency between 30 MHz and 10 GHz;
the electronic circuit has backscatter properties that vary in response to the biosignal, wherein the biosignal is generated by a biopotential that is detected by the two electrodes;
the electronic circuit is configured to transmit a backscatter signal when the electronic circuit receives the excitation signal and the biosignal; and
a characteristic of the biosignal can be determined by demodulating the backscatter signal.

2. The apparatus of claim 1, wherein the biosignal is generated by a sensor selected from the group consisting of: a chemical, biochemical, magnetic, electromagnetic, physiological, and mechanical sensor.

3. The apparatus of claim 1, wherein the electronic circuit is configured to transmit the backscatter signal wirelessly.

4. The apparatus of claim 1, wherein the characteristic of the biosignal is an amplitude of the biosignal.

5. The apparatus of claim 1, wherein the characteristic of the biosignal is a frequency of the biosignal.

6. The apparatus of claim 1, wherein the excitation signal is a radio frequency signal.

7. The apparatus of claim 1, wherein the excitation signal is a digital logic signal.

8. The apparatus of claim 1, wherein the electronic circuit further comprises an isolating resistor.

9. The apparatus of claim 1, wherein the electronic circuit is configured to receive the biosignal in vivo.

10. The apparatus of claim 9, wherein the electronic circuit is configured to be implanted in a test subject.

11. The apparatus of claim 10, wherein the electronic circuit is configured to be inserted with a needle into the test subject.

12. The apparatus of claim 10, wherein the electronic circuit is configured to pass through the lumen of a 1 millimeter syringe needle.

13. The apparatus of claim 9, wherein the electronic circuit is configured to be placed on a skin surface of a test subject.

14. The apparatus of claim 1, wherein the electronic circuit comprises a pair of varactor diodes coupled back-to-back to form an equivalent series capacitance.

15. The apparatus of claim 1, further comprising a remote exciter configured to emit the excitation signal at a frequency equivalent to a resonant frequency of the electronic circuit.

16. The apparatus of claim 1, wherein the excitation signal has a frequency between 100 MHz and 3 GHz.

17. The apparatus of claim 1, wherein the excitation signal induces a voltage between 0.5 and 5.0 volts in the electronic circuit.

18. A method of measuring a biocharacteristic, the method comprising:
providing a passive electronic circuit according to claim 1, wherein the electronic circuit is configured to measure a biopotential;
providing an excitation signal to the electronic circuit, wherein the excitation signal has a frequency between 30 MHz and 10 GHz;
generating a biosignal with the biopotential and transmitting the biosignal to the electronic circuit;
transmitting a backscatter signal from the electronic circuit; and
measuring the backscatter signal to determine a characteristic of the biosignal.

19. The method of claim 18, wherein the electronic circuit comprises a resonant frequency that is variable.

20. The method of claim 18, wherein the electronic circuit has a base resonant frequency when a biosignal is not transmitted to the electronic circuit, and wherein the excitation signal is provided at the base resonant frequency.

21. The method of claim 18, wherein the biosignal is generated by a sensor selected from the group consisting of: a chemical, biochemical, magnetic, electromagnetic, physiological, and mechanical sensor.

22. The method of claim 18, wherein the electronic circuit receives the biosignal in vivo.

23. The method of claim 22, further comprising implanting the electronic circuit subcutaneously in a test subject.

24. The method of claim 23, further comprising implanting the electronic circuit in a test subject with a needle.

* * * * *